United States Patent [19]

Matsui et al.

[11] 4,440,778

[45] Apr. 3, 1984

[54] ANTI-INFLAMMATORY ANALGESIC CATAPLASM AND PROCESS FOR PRODUCING THE SAME

[75] Inventors: Ichiro Matsui, Toyama; Tsutomu Tanaka, Kamiichi; Yukio Bando; Kiyonobu Ohashi, both of Toyama, all of Japan

[73] Assignee: Kowa Co., Ltd., Nagoya, Japan

[21] Appl. No.: 348,315

[22] Filed: Feb. 12, 1982

[30] Foreign Application Priority Data

Feb. 26, 1981 [JP] Japan ................................. 56-27199

[51] Int. Cl.$^3$ ............................................. A61K 31/40
[52] U.S. Cl. .................................................... 424/274
[58] Field of Search .......................................... 424/274

[56] References Cited

PUBLICATIONS

Chem. Abst. 94-7725q (1981).

*Primary Examiner*—Stanley J. Friedman
*Attorney, Agent, or Firm*—Oblon, Fisher, Spivak, McClelland & Maier

[57] ABSTRACT

An anti-inflammatory analgesic cataplasm is disclosed which comprises indomethacin as the active ingredient. Such cataplasm is produced by dissolving indomethacin in its non-ionic state, followed by the incorporation of water, a polyalcohol, a binder, a neutralizing agent and a vehicle, and homogenizing the resulting mixture into a paste.

4 Claims, No Drawings

ANTI-INFLAMMATORY ANALGESIC CATAPLASM AND PROCESS FOR PRODUCING THE SAME

BACKGROUND OF THE INVENTION

1. Field of the Invention

This invention relates to an anti-inflammatory analgesic cataplasm comprising indomethacin as the active ingredient, and to a process for the production of such cataplasm.

2. Description of the Prior Art

Indomethacin is a compound represented by the following formula

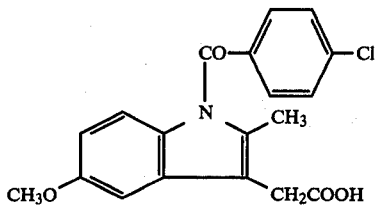

and made on record in "The Pharmacopoeia of Japan", 9th Edition. Indomethacin is known to be a non-steroid antiinflammatory drug exhibiting anti-inflammatory and analgesic activities.

As a formulation, indomethacin has been commercially available in the form of a capsule since 1966 and has found wide use for the medical treatment of rheumatoid arthritis and arthritis deformans as well as various inflammatory diseases and postoperative inflammations. Indomethacin has thus been proven to be substantially medicinally effective. When administered orally, however, indomethacin encounter many adverse effects of gastroenteric troubles such as decreased appetite, nausea, vomiting, indigestion, diarrhoea and stomach ache as well as central nervous system troubles such as frontal head ache, drowsiness, dizziness and mental disorders.

An alternative formulation resides in an indomethacin suppository for parenteral administration. Although the suppository reduces the gastroenteric troubles experienced with the capsule just discussed, it cannot be applied to a patient suffering from an intestinal disease, nor does it overcome the central nervous system troubles caused by the systemic circulation of indomethacin.

An indomethacin ointment has been developed so as to be rendered suitable for a more advanced mode of application which would avoid the central nervous system troubles and achieve any local effectiveness of indomethacin. Such ointment in fact minimizes the adverse effects noted above but is not still satisfactory in that the amount of application is difficult to hold at a constant level because of the user's arbitrary choice of dosage. Moreover, a solvent contained in the ointment is liable to evaporate during or after the application, resulting in varied formulation, so that indomethacin is hard to be absorbed through the skin and does not provide its inherently desired potency. Further inconvenience is that the user's fingers are soiled with the ointment during its application to an affected part, with eventual staining of his clothes after the application.

In many studies leading to the present invention, particular note has been taken of the fact that the absorption rate and amount of indomethacin through the skin depend largely upon the application amount and surface area of this medicine relative to any affected parts.

On the other hand, indomethacin is not subject to percutaneous absorption since a horny substance layer or stratum corneum of the skin acts as a first barrier to prevent evaporation of water and penetration of any substance from the outside and since a basal cell layer of the skin also acts as a second barrier to obstruct percutaneous absorption. Hydration of the stratum corneum can increase the penetrability of the skin by four to five times as much as usual, and hence, such hydration constitutes an important factor for percutaneous absorption of indomethacin.

It is necessary, therefore, that a substantial amount of water be added relative to a proportion of indomethacin to improve the absorbability of the medicine for use in a cataplasm.

However, indomethacin is an acidic anti-inflammatory drug (pKa 4.5) which is insoluble in water but is soluble in an alkaline solution. When dissolved in an alkaline solution, indomethacin becomes chemically unstable and readily decomposable. It is difficult to prepare an indomethacin-containing cataplasm by any conventional method employing a weakly alkaline solution. Even if mixed with and suspended in any base components, indomethacin is less stable and less absorbable through the skin in a pH range of 7 or higher wherein it is ionized. And yet, no medical treatment by indomethacin is attainable with satisfactory results.

SUMMARY OF THE INVENTION

It is, therefore, an object of the present invention to provide an anti-inflammatory analgesic cataplasm comprising indomethacin as the active ingredient which is completely devoid of the above noted difficulties of the existing indomethacin formulations.

Another object of the invention is to provide such cataplasm which is capable of being applied to any affected parts with a predetermined amount of indomethacin and achieving the desired anti-inflammatory analgesic activity of indomethacin and which is easy to apply and handle.

A further object of the invention is to provide a process for preparing such cataplasm by which indomethacin is dissolved in its non-ionic state so that it is chemically stable for a long period of time and is easily absorbable through the skin.

Briefly, these objects and other objects of the invention as will hereinafter become more readily apparent can be attained by an anti-inflammatory analgesic cataplasm comprising indomethacin as the active ingredient.

DETAILED DESCRIPTION OF THE PREFERRED EMBODIMENTS

According to the invention, an anti-inflammatory analgesic cataplasm is prepared by dissolving indomethacin in its non-ionic state, incorporating into the solution water, a polyalcohol, a binder, a neutralizing agent and a vehicle, and homogenizing the resulting mixture to form a paste having a pH of 5 to 7, and if required, spreading the paste onto a substrate.

For the dissolution of indomethacin in its non-ionic state, it is preferable to use either one or both of an aromatic alcohol and a non-ionic surfactant. Eligible examples of the aromatic alcohol include benzyl alcohol and phenethyl alcohol, whereas eligible examples of the non-ionic surfactant include a polyoxyethylene sorbitan fatty acid ester and a sorbitan fatty acid ester. Preferably, each of the aromatic alcohol and the surfactant is added in an amount of 0.5 to 5.0% (w/w). The use of these reagents makes it possible to dissolve indomethacin in a reduced volume of 1/5 to 1/10 as compared to the case where a lower alcohol such as methanol or ethanol is employed to dissolve this medicine.

Eligible examples of the polyalcohol include glycerin, polyethylene glycol, propylene glycol and sorbitol. One or more polyalcohols may be suitably used for the practice of the invention. It is desirable that the polyalcohol in an amount of 15 to 40% (w/w) be mixed with water in an amount of 20 to 55% (w/w).

By the addition of such a large amount of water, it is possible to hydrate the stratum corneum of the skin and to thereby increase the penetrability of the skin.

Eligible examples of the binder include gelatin, gum arabic, methyl cellulose, polyvinyl alcohol, hydroxyethyl cellulose, sodium polyacrylate, sodium carboxymethyl cellulose, sodium alginate, propylene glycol alginate, Santan gum and a carboxyvinyl polymer, which binders should render viscous a water-polyalcohol mixture. Each of these binders tends to reach its peak viscosity in a pH range of 8 to 9. To ensure the stability and good percutaneous absorption of indomethacin and to maintain a proper viscosity required for the cataplasm, a very small amount of an organic acid such as L-sorbic acid or gluconic acid is added as a neutralizing agent which aids in adjusting the pH of the cataplasm within a range of 5 to 7. To this end, the binder may be included in its final concentration of 10 to 20% (w/w).

Eligible examples of the vehicle include kaolin, bentonite, zinc oxide, titanium oxide and aluminum silicate which are used for conventional cataplasms.

Eligible examples of the substrate include cloth and non-woven fabric commonly used in the preparation of cataplasms.

In carrying out the invention to practice, for instance (1) with use of a portion of water, the binder is swollen and dissolved, (2) with use of the rest of water and the polyalcohol, the vehicle and other ingredients are homogeneously dispersed, (3) indomethacin is dissolved in the aromatic alcohol and/or the surfactant, (4) the resulting materials (1), (2) and (3) are homogeneously mixed to form a paste, and the paste is then spread onto a piece of cloth to obtain a cataplasm.

By the process of the invention, indomethacin can be incorporated in stable conditions in a concentration of 0.1 to 5.0% (w/w).

The medicinal activities of the anti-inflammatory analgesic cataplasm containing indomethacin, as prepared by the above process, will now be described.

Inhibition tests against carragheenin foot bottom edema, adjuvant foot bottom edema and inflammation foot pressure pain were conducted in order to assay the medicinal activities of the anti-inflammatory analgesic cataplasm of the invention. At the same time, an irritation test on the skin was done to confirm the safety of the cataplasm.

The inhibition test against carragheenin foot bottom edema was carried out with use of some groups of Wister male rats having a weight of 100 to 140 g, each group consisting of 15 rats. The volume of a right side hind foot bottom of each rat was measured by a volume measuring device using a pressure transducer. As an inflammation-inducing agent, 0.1 ml of a 2% carragheenin (Minseirika Co.) physiological sodium chloride solution was then injected hypodermically to the right side hind foot bottom. Immediately thereafter, an anti-inflammatory analgesic cataplasm prepared in Example 1 described hereinafter and having a size of 2.5×2.5 cm was placed on the inflamed foot bottom which was then covered with an elastic bandage to prevent the cataplasm from being licked by the rat. 4 hours later, the cataplasm was removed, and the foot bottom edema volume was measured. Only carragheenin was injected to a control group of rats. For purposes of comparison, use was made of an indomethacin ointment (containing 1.0% of indomethacin) prepared in Comparative Example 1 given below and a common cataplasm (containing l-methanol and camphor) prepared in Comparative Example 2 given below.

The edema rates were calculated by the following equation.

$$\text{Edema rate} = \frac{V_4 - V_0}{V_0} \times 100 \, (\%)$$

$V_0$: Foot bottom volume prior to carragheenin injection $V_4$: Foot bottom volume upon expiration of 4 hours after carragheenin injection The inhibition rates were calculated by the following equation.

$$\text{Inhibition rate} = \frac{Ec - Ea}{Ec} \times 100 \, (\%)$$

$Ec$: Edema rate of control group
$Ea$: Edema rate of administered group
The results obtained are shown in Table 1.

TABLE 1

| Drugs | Inhibition effects against the carragheenin foot bottom edema | | | |
|---|---|---|---|---|
| | Number of rats | Amounts of administration | Edema rates (%) | Inhibition rates (%) |
| Control (untreated) | 15 | — | 92.9 ± 4.5 | — |
| Anti-inflammatory analgesic cataplasm | | | | |
| (0.5%) | 15 | 2.5 cm × 2.5 cm | 63.5 ± 4.1 | 31.6 |
| (1.0%) | 15 | " | 41.4 ± 4.4 | 55.4 |
| (2.0%) | 15 | " | 37.2 ± 6.2 | 60.0 |
| Indomethacin ointment (1.0%) | 15 | 100 mg | 71.6 ± 5.8 | 22.9 |
| Cataplasm (common) | 15 | 2.5 cm × 2.5 cm | 78.9 + 6.4 | 15.1 |

The anti-inflammatory analgesic cataplasm containing 0.5% of indomethacin exhibited a higher inhibition rate than the indomethacin ointment. As regards the same rate, the other cataplasms containing 1.0% or more of indomethacin were twice or more as high as the indomethacin ointment.

The inhibition test against the adjuvant foot bottom edema was conducted with use of some groups of Wister male rats having a weight of 120 to 180 g, each group consisting of 20 rats. Observing the procedure described in the previous or first test, the volume of a right side hind foot bottom of each rat was measured by a volume measuring device using a pressure transducer. As an inflammation-inducing agent, a liquid paraffin solution of mycobacterium (Difco Co.) was hypodermically injected to the right side hind foot bottom in a dosage of 0.3 mg/0.05 ml. Immediately after the injection, an anti-inflammatory analgesic cataplasm (2.5×2.5 cm) prepared in Example 1 was placed on the inflamed part which was then covered with an elastic bandage in the same manner as in the first test. The test drug was applied for 8 hours a day for 21 days. Thereafter, the volume of the foot bottom edema was measured. Only an adjuvant was injected to control rats. For purposes of comparison, use was made of an indomethacin ointment (containing 1.0% of indomethacin) and a common cataplasm (containing l-menthol and camphor). The edema and inhibition rates were calculated in the same manner as in the first test.

The results obtained are shown in Table 2.

TABLE 2

Inhibition effects against the adjuvant foot bottom edema

| Drugs | Number of rats | Amounts of administration | Edema rates (%) | Inhibition rates (%) |
|---|---|---|---|---|
| Control (untreated) | 20 | — | 229.2 ± 13.0 | — |
| Anti-inflammatory analgesic cataplasm | | | | |
| (0.5%) | 20 | 2.5 cm × 2.5 cm | 158.0 ± 11.6 | 31.1 |
| (1.0%) | 20 | " | 137.0 ± 11.2 | 40.0 |
| (2.0%) | 20 | " | 88.9 ± 10.3 | 61.2 |
| Indomethacin ointment (1.0%) | 20 | 100 mg | 171.2 ± 18.7 | 25.3 |
| Cataplasm (common) | 20 | 2.5 cm × 2.5 cm | 204.5 ± 17.1 | 10.8 |

The anti-inflammatory analgesic cataplasms were 3 to 6 times as effective as the common cataplasm. Those containing 1.0% or more of indomethacin exhibited an anti-inflammatory activity of 1.5 to 2 times greater than that of the indomethacin ointment.

The inhibition test against the inflammation foot pressure pain was conducted by a Randall-Selto method. Namely, some groups of Wister male rats having a weight of 120 to 140 g were used, each group consisting of 10 rats. 0.1 ml of a 2% carragheenin physiological sodium chloride solution was hypodermically injected to a right side hind foot bottom. Immediately thereafter, an anti-inflammatory analgesic cataplasm (2.5×2.5 cm) prepared in Example 1 was placed on the inflamed part which was then covered with an elastic bandage. 4 hours later, the cataplasm was removed. The inflamed foot bottom was pressed by a hydraulic analgesic tester (Natsume Seisakusho), and the pain value was determined based on the avoidance response. Only carragheenin was injected to control rats. For purposes of comparison, use was made of an indomethacin ointment and a common cataplasm, both of which were similar to those used in the first and second tests.

The increasing rates of pain values were calculated by the following equation.

$$\text{Increasing rate of pain value} = \frac{Pa - Pc}{Pc} \times 100\ (\%)$$

Pc: Pain value of control group
Pa: Pain value of administered group

The results obtained are shown in Table 3.

TABLE 3

Inhibition effects against inflammation foot pressure pain

| Drugs | Number of rats | Amounts of administration | Pain values (m ± S.E.) | Increasing rates of pain values (%) |
|---|---|---|---|---|
| Control (untreated) | 10 | — | 0.312 ± 0.012 | — |
| Anti-inflammatory analgesic cataplasm | | | | |
| (0.5%) | 10 | 2.5 cm × 2.5 cm | 0.392 ± 0.021 | 25.6 |
| (1.0%) | 10 | 2.5 cm × 2.5 cm | 0.476 ± 0.018 | 52.6 |
| (2.0%) | 10 | 2.5 cm × 2.5 cm | 0.523 ± 0.025 | 67.6 |
| Indomethacin ointment (1.0%) | 10 | 100 mg | 0.370 ± 0.027 | 18.6 |
| Cataplasm (common) | 10 | 2.5 cm × 2.5 cm | 0.334 ± 0.020 | 7.1 |
| Normal | 8 | — | 1.030 + 0.019 | — |

The anti-inflammatory analgesic cataplasms exhibited an analgesic activity of 3.5 to 9.5 times greater than that of the common cataplasm. Further, the one having the same indomethacin content as the ointment was about 3 times as high as the ointment in terms of this activity.

The irritation test on the skin was conducted with use of some groups of female rabbits having a weight of 2.0 to 2.5 kg, each group consisting of 5 rabbits. The skin irritation coefficients upon expiration of 24, 48 and 72 hours after the placement of anti-inflammatory analgesic cataplasms were determined in accordance with the evaluation standards of Ikeda et al. [Study on Pharmaceuticals, Vol. 1, No. 116 (1970)] with respect to a normal skin group of rabbits on which an anti-inflammatory analgesic cataplasm prepared in Example 1 was placed 24 hours after hair cutting with an electric hair cutter, and to a stratum corneum-peeled group of rabbits on which the above anti-inflammatory analgesic cataplasm was placed after hair cutting with an electric hair cutter, followed by hair removal with a depilatory agent (Ever Cream, Tanabe Pharmaceutical Co.) and by peeling of the stratum corneum with a scotch tape (Cellotape, Nichiban Co.). A common cataplasm similar to those of the foregoing three tests was used as a comparation drug.

The results obtained are shown in Table 4.

TABLE 4

Results of the irritation test on the skin

| Drugs | Time after placement (hours) | Skin irritation coefficients* Normal skin group | Stratum corneum-peeled group |
|---|---|---|---|
| Anti-inflammatory analgesic cataplasm (1.0% of indomethacin) | 24 | 0 | 0.4 ± 0.24 |
| | 48 | 0 | 0.2 ± 0.20 |
| | 72 | 0 | 0 |
| Anti-inflammatory analgesic cataplasm (2.0% of indomethacin) | 24 | 0 | 0.4 ± 0.24 |
| | 48 | 0 | 0.2 ± 0.20 |
| | 72 | 0 | 0 |

TABLE 4-continued

Results of the irritation test on the skin

| Drugs | Time after placement (hours) | Skin irritation coefficients* | |
|---|---|---|---|
| | | Normal skin group | Stratum corneum-peeled group |
| Cataplasm (common) | 24 | 0 | 2.4 ± 0.24 |
| | 48 | 0 | 1.5 ± 0.26 |
| | 72 | 0 | 0.8 ± 0.37 |

*The irritation coefficients were determined in accordance with the standards by Ikeda et al.

The anti-inflammatory analgesic cataplasms were by far smaller in the skin irritation coefficients than the common cataplasm.

In order to demonstrate the medicinal effectiveness of an anti-inflammatory analgesic cataplasm of the invention, clinical studies were conducted with respect to 46 cases. A cataplasm prepared in Example 3 was selected for these studies.

The results obtained are shown in Table 5.

TABLE 5

Results of the clinical studies

| Diseases | Grades* | | | | | Number of diseases |
|---|---|---|---|---|---|---|
| | A | B | C | D | E | |
| Arthrosis deforman | 0 | 1 | 3 | 0 | 0 | 4 |
| Rheumatoid arthritis | 0 | 0 | 1 | 0 | 0 | 1 |
| Subtotal | 0 | 1(20.0%) | 4(80.0%) | 7(15.2%) | 0 | 5 |
| Tendinitis tenosynovitis | 1 | 2 | 0 | 0 | 0 | 3 |
| Cervical syndrome | 0 | 3 | 2 | 3 | 0 | 8 |
| Epcondylytis | 1 | 2 | 2 | 1 | 0 | 6 |
| Myalgia | 1 | 6 | 5 | 3 | 0 | 15 |
| Subtotal | 3(9.4%) | 13(40.6%) | 9(28.1%) | 7(21.9%) | 0 | 32 |
| Fracture | 0 | 1 | 1 | 0 | 0 | 2 |
| Distorsion | 2 | 2 | 1 | 0 | 0 | 5 |
| Contusion | 2 | 0 | 0 | 0 | 0 | 2 |
| Subtotal | 4(44.4%) | 3(33.3%) | 2(22.2%) | 0 | 0 | 9 |
| Total | 7(15.2%) | 17(37.0%) | 15(32.6%) | 7(15.2%) | 0 | 46 |

*The grading notations of effectiveness are as follows:
A: Fully efficacious
B: Fairly efficacious
C: Efficacious
D: Inefficacious
E: Ingravescent The anti-inflammatory analgesic cataplasm of the invention contains a predetermined amount of indomethacin in substantially stable conditions in the presence of a larger amount of water. Accordingly, such cataplasm imparts ready hydration of the stratum corneum to the skin, coupled with the covering effect of the cloth on any affected parts, and facilitates the absorption of indomethacin through the skin to the affected parts. It is clear from the above results of various tests for medicinal activities that the cataplasm has an anti-inflammatory analgesic potency of 3 to 7 times greater than that of the commercially available cataplasm and of 2 to 3 times greater than that of the indomethacin ointment. Further, the cataplasm of the invention gives little irritation to the skin and is easy to handle, for instance, in its placement on or removal from the skin.

The anti-inflammatory analgesic cataplasm of the invention enables a desired amount of indomethacin to be percutaneously safely absorbed by any affected parts while preventing occurrence of adverse effects of indomethacin upon the digestive and central nervous systems. Thus, it is important to note that the cataplasm of the invention can utilize the excellent anti-inflammatory analgesic activity of indomethacin to its maximum extent.

The process according to the invention is particularly advantageous in that a cataplasm can be prepared with indomethacin being kept stable for an extended period of time even in the presence of a substantial amount of water, the active ingredient being otherwise insoluble in water and unstable in an alkaline solution. The process involves simplified steps and brings about mass production with low cost.

This invention will now be described in further detail with reference to certain specific examples which are provided for purposes of illustration only and are not to be construed as limiting to the invention.

EXAMPLE 1

| Composition: | |
|---|---|
| (1) Indomethacin | 1.0 g |
| (2) Natural aluminum silicate | 8.0 g |
| (3) Gelatin | 8.0 g |
| (4) Sodium polyacrylate | 1.0 g |
| (5) Carboxyvinyl polymer | 0.5 g |
| (6) Sodium alginate | 2.5 g |
| (7) Glycerin | 20.0 g |
| (8) Polyethylene glycol 400 | 2.0 g |
| (9) Polyoxyethylene sorbitan monooleate | 3.0 g |
| (10) Benzyl alcohol | 2.0 g |
| (11) Gluconic acid solution (50%) | 1.0 g |
| (12) Purified water | 51.0 g |
| Total | 100.0 g |

Process:

(A) To materials (3), (5), (6) and (11) was added 51.0 g of purified water (12), and the mixture was heated and dissolved.

(B) To material (7) were added materials (2) and (4), and the mixture was dispersed with stirring.

(C) To materials (8), (9) and (10) was added material (1) and the mixture was heated, stirred and dissolved.

(D) To mixture (A) was added mixture (B), and the admixture was kneaded and stirred, followed by the addition of mixture (C), until it became homogeneous.

(E) The paste thus obtained was spread onto cloth which was then covered with a polyethylene film to prepare an anti-inflammatory analgesic cataplasm.

When indomethacin is incorporated in an amount of 0.5 or 2.0 g, a water content should be 51.5 g or 50.0 g, respectively. A cataplasm can be prepared in the same manner as just stated.

EXAMPLE 2

| Composition: | |
|---|---|
| (1) Indomethacin | 0.5 g |
| (2) Zinc oxide | 8.0 g |
| (3) Gelatin | 3.0 g |
| (4) Sodium polyacrylate | 1.0 g |
| (5) Carboxyvinyl polymer | 1.0 g |

| Composition: | |
|---|---|
| (6) Sodium carboxymethyl cellulose | 2.0 g |
| (7) Glycerin | 10.0 g |
| (8) Sorbitol solution (70%) | 15.0 g |
| (9) Polyethylene glycol 400 | 3.0 g |
| (10) Polyoxyethylene sorbitan monooleate | 2.0 g |
| (11) Benzyl alcohol | 1.0 g |
| (12) Purified water | 53.5 g |
| Total | 100.0 g |

Process:

(A) To materials (3), (5), (6) and (8) was added 53.5 g of purified water (12), and the mixture was heated and dissolved.

(B) To material (7) were materials (2) and (4), and the mixture was dispersed with stirring.

(C) To materials (9), (10) and (11) was added material (1), and the mixture was heated, stirred and dissolved.

(D) To mixture (A) was added mixture (B), and the admixture was kneaded and stirred, followed by the addition of mixture (C), until it became homogeneous.

(E) The paste thus obtained was spread onto cloth which was then covered with a polyethylene film to prepare an anti-inflammatory analgestic cataplasm.

EXAMPLE 3

| Composition: | |
|---|---|
| (1) Indomethacin | 1.0 g |
| (2) Titanium oxide | 2.0 g |
| (3) Kaolin | 15.0 g |
| (4) Gelatin | 2.0 g |
| (5) Sodium polyacrylate | 4.0 g |
| (6) Lactic acid | 3.0 g |
| (7) Glycerin | 18.0 g |
| (8) Sorbitol solution (70%) | 10.0 g |
| (9) Polyethylene glycol 400 | 1.0 g |
| (10) Diisopropyl adipate | 2.0 g |
| (11) Benzyl alcohol | 1.5 g |
| (12) Sorbitan monooleate | 0.5 g |
| (13) Polyoxyethylene sorbitan monooleate | 0.5 g |
| (14) Purified water | 39.5 g |
| Total | 100.0 g |

Process:

(A) To materials (2), (3), (4), (6) and (8) was added 39.5 g of purified water (14), and the mixture was heated and suspended.

(B) To material (7) was added material (5), and the mixture was dispersed with stirring.

(C) To materials (9), (10), (11), (12) and (13) was added material (1), and the mixture was heated, stirred and dissolved.

(D) To mixture (A) was added mixture (B), and the admixture was kneaded and stirred, followed by the addition of mixture (C), until it became homogeneous.

(E) The paste thus obtained was spread onto cloth which was then covered with a polyethylene film to prepare an anti-inflammatory analgesic cataplasm.

EXAMPLE 4

| Composition: | |
|---|---|
| (1) Indomethacin | 5.0 g |
| (2) Kaolin | 15.0 g |
| (3) Gelatin | 2.0 g |
| (4) Sodium polyacrylate | 4.0 g |
| (5) Propylene glycol alginate | 1.0 g |
| (6) Lactic acid | 3.0 g |
| (7) Glycerin | 16.0 g |
| (8) Polyethylene glycol 400 | 17.0 g |
| (9) Sorbitol solution (70%) | 10.0 g |
| (10) Phenethyl alcohol | 1.5 g |
| (11) Sorbitan monooleate | 1.0 g |
| (12) Purified water | 24.5 g |
| Total | 100.0 g |

Process:

(A) To materials (2), (3), (5), (6) and (9) was added 24.5 g of purified water (12), and the mixture was heated and suspended.

(B) To material (7) was added material (4), and the mixture was dispersed with stirring.

(C) To materials (8), (10) and (11) was added material (1), and the mixture was heated, stirred and dissolved.

(D) To mixture (A) was added mixture (B), and the admixture was kneaded and stirred, followed by the addition of mixture (C), until it became homogeneous.

(E) The paste thus obtained was spread onto cloth which was then covered with a polyethylene film to prepare an anti-inflammatory analgesic cataplasm.

COMPARATIVE EXAMPLE 1 (INDOMETHACIN OINTMENT)

| Composition: | |
|---|---|
| (1) Carboxyvinyl polymer | 1.0 g |
| (2) Hydroxyethyl cellulose | 1.0 g |
| (3) Indomethacin | 1.0 g |
| (4) Polyethylene glycol 300 | 10.0 g |
| (5) Ethanol | 30.0 g |
| (6) Triethanolamine | 4.0 g |
| (7) Purified water | 53.0 g |
| Total | 100.0 g |

Process:

(A) Materials (1) and (2) were swollen in 20 g of purified water.

(B) Material (3) was dissolved in materials (4) and (5).

(C) To mixture (A) was added mixture (B), and the admixture was stirred until it was completely hydrated.

(D) To 10 g of purified water was added material (6), and the mixture was stirred, followed by the addition of mixture (C) and the rest of purified water, until it became homogeneous.

COMPARATIVE EXAMPLE (CATAPLASM CONTAINING L-MENTHOL AND CAMPHOR)

| Composition: | |
|---|---|
| (1) Peppermint oil | 1.5 g |
| (2) dl-Camphor | 1.0 g |
| (3) Thymol | 0.1 g |
| (4) Zinc oxide | 10.0 g |
| (5) Gelatin | 3.0 g |
| (6) Sodium polyacrylate | 8.0 g |
| (7) Sodium alginate | 3.0 g |
| (8) Sorbitan fatty acid ester | 1.0 g |
| (9) Glycerin | 25.0 g |
| (10) Purified water | 47.4 g |
| Total | 100.0 g |

Process:

(A) To material (10) were added materials (5) and (7), and the mixture was heated and dissolved.

(B) To material (8) were added materials (1), (2), (3) and (4), and the mixture was stirred.

(C) To material (9) was added material (6), and the mixture was stirred and dissolved.

(D) To mixture (A) was added mixture (C), and the admixture was stirred until it became homogeneous.

Having now fully described this invention, it will be apparent to one of ordinary skill in the art that many changes and modifications can be made thereto without departing from the spirit or scope of the invention as set forth herein.

What is claimed is:

1. An anti-inflammatory analgesic cataplasm comprising:

indomethacin in the range of from 0.1 to 5.0 by weight;

a polyalcohol selected from the group consisting of glycerin, polyethylene glycol, propylene glycol and sorbitol;

a binder selected from the group consisting of gelatin, gum arabic, methyl cellulose, polyvinyl alcohol, hydroxyethyl cellulose, sodium polyacrylate, sodium carboxymethyl cellulose, sodium alginate, propylene glycol alginate, santan gum and a carboxyvinyl polymer;

a vehicle selected from the group consisting of kaolin, bentonite, zinc oxide, titanium oxide and aluminum silicate;

an aromatic alcohol selected from the group consisting of benzyl alcohol and phenethyl alcohol, or a non-ionic surfactant selected from the group consisting of polyoxyethylene sorbitan fatty acid ester and a sorbitan fatty acid ester or mixtures of said aromatic alcohol and said non-ionic surfactants; and water, said cataplasm having a pH of 5 to 7.

2. The anti-inflammatory analgesic cataplasm according to claim 1, said polyalcohol being presented in the range of from 15 to 40% by weight, said binder in the range of from 10 to 20% by weight, said vehicle in the range of 10–20% by weight, and said aromatic alcohol, non-ionic surfactant or mixture of said aromatic alcohol and said non-ionic surfactant in the range of from 0.5 to 5.0% by weight, respectively, in the cataplasm.

3. A process for producing an anti-inflammatory analgesic cataplasm, comprising the steps of dissolving indomethacin in its non-ionic state, incorporating into the solution water, a polyalcohol, a binder, a neutralizing agent and a vehicle, and homogenizing the resulting mixture to form a paste, and if required, spreading said paste onto a substrate.

4. The process as claimed in claim 3, said dissolving step being effected by dissolving said indomethacin in either one or both of an aromatic alcohol and a surfactant.

* * * * *